United States Patent
Smith et al.

(10) Patent No.: US 9,913,620 B2
(45) Date of Patent: Mar. 13, 2018

(54) TILTING HEAD SUPPORT FOR MEDICAL IMAGING

(71) Applicant: GENERAL ELECTRIC COMPANY, Schenectady, NY (US)

(72) Inventors: Chad Allan Smith, Waukesha, WI (US); John Moore Boudry, Waukesha, WI (US); Brandon Allan Smith, Waukesha, WI (US); Jaime Lehrer, Milwaukee, WI (US)

(73) Assignee: General Electric Company, Schenectady, NY (US)

(*) Notice: Subject to any disclaimer, the term of this patent is extended or adjusted under 35 U.S.C. 154(b) by 317 days.

(21) Appl. No.: 14/754,025

(22) Filed: Jun. 29, 2015

(65) Prior Publication Data

US 2016/0374630 A1 Dec. 29, 2016

(51) Int. Cl.
*A61B 6/04* (2006.01)
*A61B 6/00* (2006.01)
*A61B 6/03* (2006.01)

(52) U.S. Cl.
CPC ............ *A61B 6/0407* (2013.01); *A61B 6/501* (2013.01); *A61B 6/032* (2013.01); *A61B 6/037* (2013.01)

(58) Field of Classification Search
CPC .................................. A61G 15/12; A61G 6/04
USPC ...................................................... 5/621–622
See application file for complete search history.

(56) References Cited

U.S. PATENT DOCUMENTS

| | | |
|---|---|---|
| 4,266,759 A | 5/1981 | Liebman |
| 4,400,820 A | 8/1983 | O'Dell et al. |
| 4,616,814 A | 10/1986 | Harwood-Nash et al. |
| 5,233,713 A | 8/1993 | Murphy et al. |
| 6,684,431 B2 | 2/2004 | Splane, Jr. |
| 7,909,036 B2 | 3/2011 | Kusner, Jr. et al. |
| 8,887,331 B2 | 11/2014 | Nakamura et al. |
| 2013/0098376 A1* | 4/2013 | Hunter, Jr. ............ A61F 5/3761 128/878 |

* cited by examiner

Primary Examiner — Fredrick C Conley

(57) ABSTRACT

A tilting head support for use in medical imaging is described. The tilting head support allows a patient to receive the equivalent of a tilted gantry exam study even when using a scanner gantry that does not tilt. In certain embodiments, the tilted head support assembly has metallic or sharp edge components, if present, positioned outside the imaging area when in use. In addition, in certain embodiments, the tilted head support assembly allows for user selection of a tilt angle from among a continuous range of available angles.

20 Claims, 5 Drawing Sheets

TILTING HEAD SUPPORT FOR MEDICAL IMAGING

BACKGROUND

The subject matter disclosed herein relates to medical imaging and, in particular, to the use of a device to support and tilt a patient's head during imaging.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a patient's body. In CT systems a detector array, including a series of detector elements, produces similar signals through various positions as a gantry is displaced around a patient, allowing volumetric reconstructions to be obtained.

Traditionally, CT scanners have had gantries that tilt with respect to the patient, allowing the scanner to image a patient's head (including the brain) and to avoid directing X-ray radiation toward the patient's eyes by way of the tilt. However, newer CT scanners rotate at higher speeds (e.g., more than two rotations per second) and have larger imaging detectors in order to better image the patient's heart. To accommodate these higher rotational speeds and the area-type detectors (as opposed to the multi-row detectors used in preceding generations), newer scanners may no longer have the ability to tilt the gantry. That is, the mechanical stresses and/or structural requirements to support higher rotational speeds and/or whole organ imaging may inconsistent with geometries that allow tilting the gantry.

BRIEF DESCRIPTION

In one embodiment, a head support attachment for use in image acquisition is provided. In accordance with this embodiment, the head support attachment includes an engagement structure configured to removably attach the head support attachment to an end of a patient support table. A head support surface is pivotally connected to the engagement structure at a first end of the head support surface. An adjustment arm is pivotally connected at a first end to the engagement structure and slidably engaged with the head support surface at a second end of the adjustment arm. An adjustment mechanism comprising a threaded assembly is configured to adjust the position of the second end of the adjustment arm so as to determine the position of the adjustment arm relative to the head support surface.

In a further embodiment, a head support attachment for use in image acquisition is provided. In accordance with this embodiment, the head support attachment includes a head support surface comprising an imaged region and a non-imaged region, the imaged region comprising a first pivoting engagement and the non-imaged region comprising a sliding engagement. A table engagement structure is attached to the head support surface at the first pivoting engagement such that the head support surface pivots relative to the table engagement structure at the first pivoting engagement. An adjustment arm is attached to the table engagement structure at a second pivoting engagement and attached to the head support surface at the sliding engagement. An adjustment mechanism underlies the non-imaged region of the head support surface. The adjustment mechanism comprises an adjustment thread configured to move a movable adjustment block within the sliding engagement. The position of the movable adjustment block adjusts the position of the adjustment arm within the sliding engagement to control the tilt of the head support surface relative to the table engagement structure.

In an additional embodiment, a patient support is provided. In accordance with this embodiment, the patient support includes a support table comprising a first end and a second end. The patient support also includes a head support attached to the first end of the support table. The head support comprises an engagement structure configured to attach to the first end of the support table and a head support surface comprising an imaged region proximate to the support table and a non-imaged region distal from the support table. The imaged region comprises a first pivoting engagement to the engagement structure and the non-imaged region comprises a sliding engagement. An adjustment arm pivotally connects at a first end to the engagement structure and attaches to the head support surface at the sliding engagement. An adjustment mechanism underlies the non-imaged region of the head support surface. The adjustment mechanism comprises an adjustment thread configured to move a movable adjustment block within the sliding engagement. The position of the movable adjustment block adjusts the position of the adjustment arm within the sliding engagement to control the tilt of the head support surface relative to the support table.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
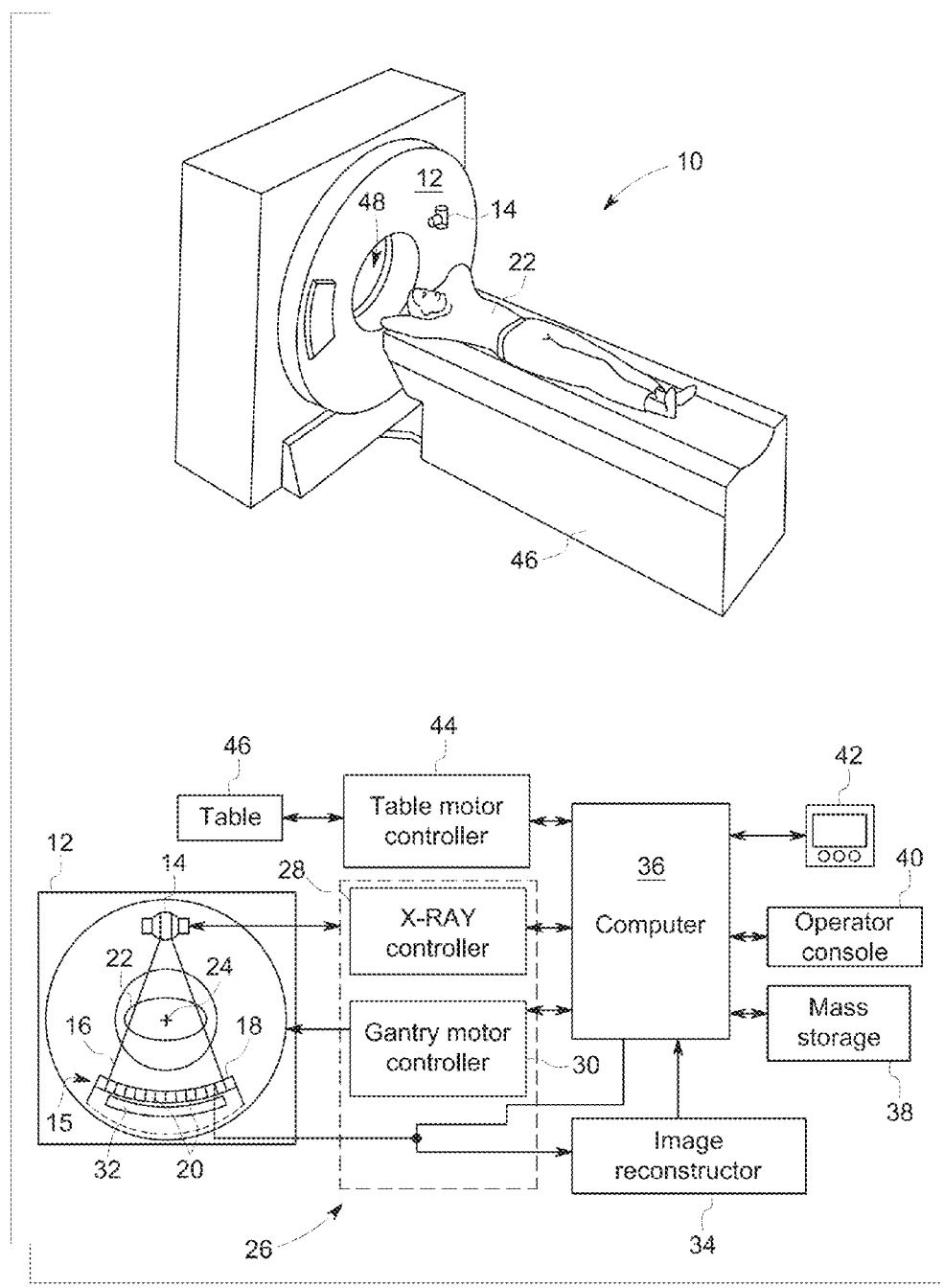
FIG. 1 is a combined pictorial view and block diagram of a computed tomography (CT) imaging system as discussed herein.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As described herein, in certain instances a CT scanner (or a positron emission tomography (PET) scanner) may be provided with a gantry that does not support tilted configurations. In such scanners, the geometries available to scan a patient's head and brain may be limited. To address this limitation of the scanner, other means may be introduced, as discussed herein, for tilting the patient's head during imaging. Various approaches, however, have limitations. For example, devices placed on the patient cradle itself (i.e., on the patient support table) may limit the available table length available for certain patients (e.g. tall patients). Such configurations also image the patient's head through the full cross-section of the material forming the patient cradle, increasing the needed X-ray power to generate good signal. Soft material designs (e.g., foam pillows) are unsuitable for replicating a given position of the patient's head in repeated exams or treatments.

Other approaches involve cantilevered designs in which the head support is cantilevered with respect to the end of the patient support table. Such designs, however, may place the tilting mechanism near the patient's neck which, while suitable for adjustment purposes, may be unsuitable for imaging purposes due to pivoting and/or locking mechanisms being proximate to the neck area and potentially interfering with imaging, such as due to introducing metal parts and/or sharp edges into the imaging path. Alternatively, designs that forgo metal components within the mechanism proximate to the neck typically substitute a simplified design that may only provide a limited number of fixed-angle positions (e.g., at 5° intervals) rather than a full range of adjustable positions. Such designs may also require the patient to move or lift their head during adjustment, may not securely lock into position (such as in the event the patient lifts their head while strapped to the head support), and may also potentially require adjustment from more than one side.

In contrast to these designs, the presently contemplated CT or PET tilting head support design utilizes a variable tilting mechanism placed outside of the imaging region of the head or brain. Such a configuration allows an operator to perform a full body scan (i.e., head to toe) of a patient while utilizing the device. Embodiments of the presently contemplated tilting head support also allow adjustment over a continuous range of angles (e.g., 0° to 30° or −10° to 35°), the ability to reproduce a given angular position in subsequent imaging sessions, the ability to raise or lower the patient's head while supported by the device, and the ability to adjust the tilt angle with a single hand from either side of the patient.

With the preceding in mind and referring to FIG. 1, a computed tomography (CT) imaging system 10 is shown, by way of example, as including a non-tilting gantry 12. The gantry 12 has an X-ray source 14 that projects a beam of X-rays 16 toward a detector assembly 15 on the opposite side of the gantry 12. The detector assembly 15 includes a collimator assembly 18, a plurality of detector modules 20, and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position patient 22 and gantry 12. Particularly, table 46 moves portions of patient 22 through a gantry opening 48.

Figure 2:
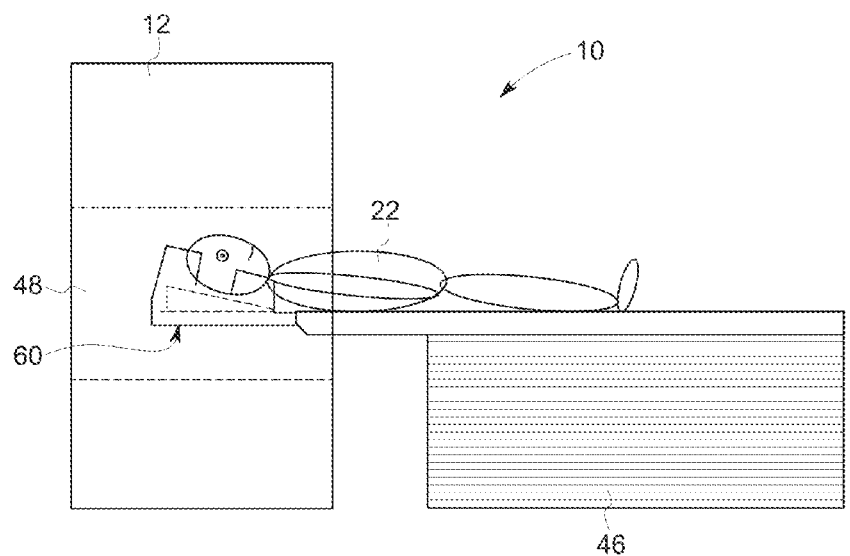
FIG. 2 depicts a diagrammatic view of a patient employing a tilted head support assembly within a CT scanner, in accordance with aspects of the present description.

As noted above, the depicted gantry 12 is described as not being capable of tilting with respect to the patient 22. This is in contrast to other CT systems in which the gantry 12 could be tilted for all or part of an imaging session, such as to image a patient's head or brain in a tilted orientation. To address this inability of the depicted CT system 10 to tilt, a head support assembly 60 capable of tilting is described herein. A representation of the use of such a head support assembly 60 in the context of a CT system 10 and patient 22 is shown in FIG. 2. In the depicted example, the head support assembly 60 is provided as a separate attachment to the patient support table 46 and may be secured to an end of the table 46 when in use. When in use, as shown, the head support assembly 60 holds the patient's head at an angle relative to the gantry 12, which corresponds to the tilt that might be possible if the gantry 12 could be tilted. Various methods of securing the support assembly 60 to the table 46, as discussed in greater detail below, may be employed.

Figure 3:
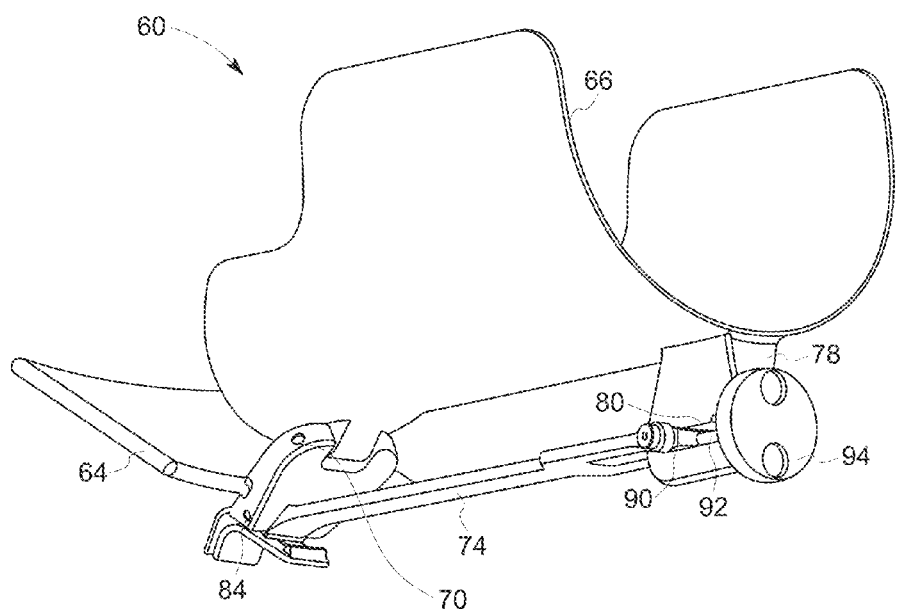
FIG. 3 depicts a perspective view of a tilting head support assembly, in accordance with aspects of the present description.
Figure 4:
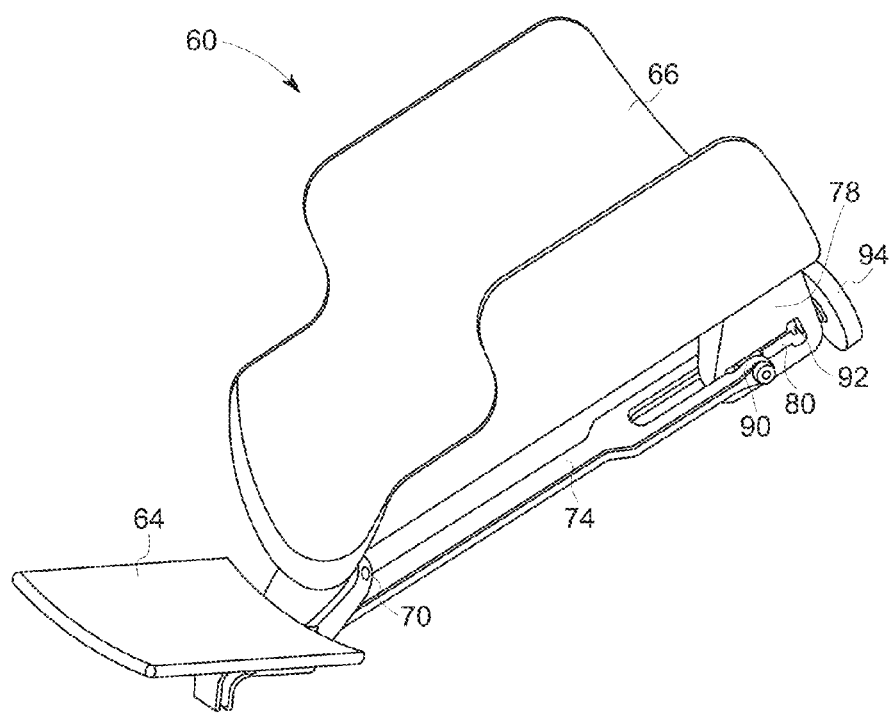
FIG. 4 depicts another perspective view of a tilting head support assembly, in accordance with aspects of the present description.
Figure 5:
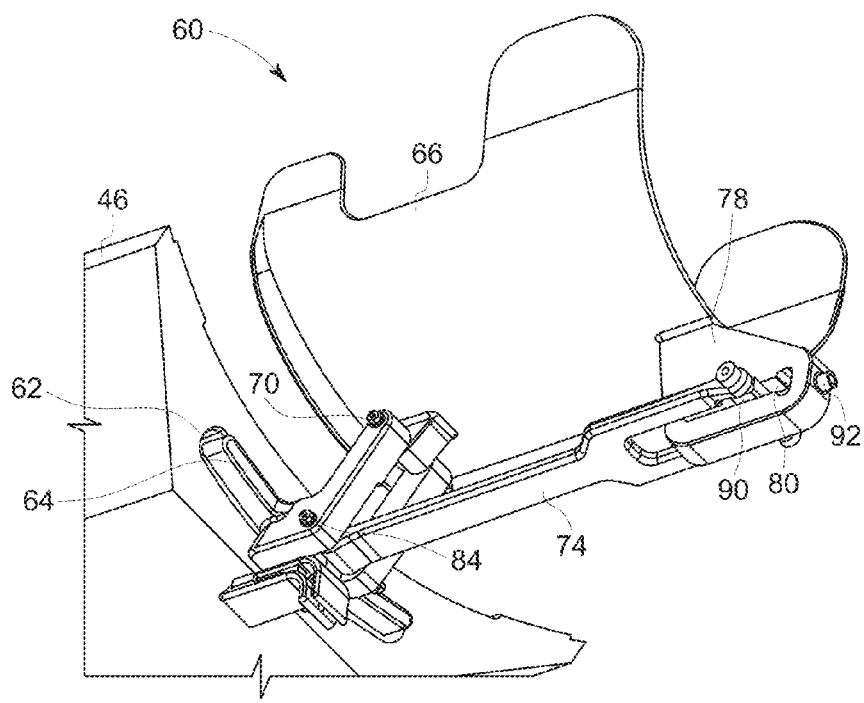
FIG. 5 a perspective view of a tilting head support assembly engaged with a CT examination table, in accordance with aspects of the present description.

With respect to implementations of a head support assembly 60, and turning to FIGS. 3-5, perspective views of one or more embodiments are depicted which may be suitable for use in a CT or PET context. By way of a non-limiting example, FIGS. 3-5 depict the support 60 as having a sliding engagement structure 64 suitable for being inserted into a complementary slot 62 (FIG. 5) formed at the end of the table 46 so as to form a cantilevered interface when so engaged. In such an embodiment, the engagement structure 64 may be made from a non-metallic, or otherwise X-ray transmissive material (e.g., plastic or carbon fiber), so as to prevent interference with the imaging process (e.g., artifact formation).

In the depicted example, the engagement structure 64, which remains stationary when in use, is connected to a tilting head support surface 66 that is configured to pivot (e.g., via non-metallic pivot pin 70) with respect to the engagement structure 64. In the depicted examples of FIGS. 3 and 4, the head support is tilted at an angle of 30° with respect to the engagement structure 64. The tilting head support surface 66 is configured to support the head of the patient during imaging and to be adjustable during the process. In certain embodiments, the head support surface 66 is also made of a non-metallic, X-ray transmissive material (e.g., plastic or carbon fiber) so as to not interfere with imaging of the head and brain. Straps (e.g., Velcro straps) may be employed to secure one or both of the patient's chin or forehead to the head support surface 66 during imaging. With this in mind, in certain embodiments such straps may be provided integral with the support surface 66 or surfaces or channels may be provided to accommodate straps that are not integral to the support surface 66.

In certain embodiments, an adjustment arm 74 acts as a linkage between the engagement structure 64 and an adjustment mechanism, discussed in greater detail below. By way of example, the adjustment arm 74 may be pivotally fixed (e.g., such as using a non-metallic pivot pin 84) to the engagement structure 64 and on another end, slidably engaged with the head support surface 66 (such as via a support block 78, discussed below) so as to transfer the support load from the adjustment mechanism to the engagement structure 64. The position of the adjustment arm 74 relative to the support block 78, and thus to the head support surface 66, may be determined by the adjustment mechanism, which in the depicted example serves to determine the extent to which the adjustment arm 74 extends into a slot 80 of the support block 78. As with other components that may extend into the imaged volume, the adjustment arm 74 may also be made of a non-metallic, X-ray transmissive material (e.g., plastic or carbon fiber) so as to not interfere with imaging process.

With respect to the support block 78, this component of the support assembly 60 may be formed integrally with the head support surface 66 (such as molded with the support surface 66) or may be a separate component that is attached (e.g., using screws (or other fasteners) or glue (or other adhesives) to the support surface 66. In certain embodiments, the support block 78 provides the translating interface between the adjustment arm 74 and a movable adjustment block 90 (or other structure that interfaces between a user-operated adjustment mechanism and the adjustment arm 74).

With respect to the user-operated adjustment mechanism, in certain embodiments, such as that depicted in FIGS. 3-5, the movable adjustment block 90 has a threaded engagement with an adjustment thread 92 (e.g., a threaded rod or bar) connected to an adjustment knob 94. In such an embodiment, rotation of the adjustment thread 92, such as by a user turning attached adjustment knob 94, causes translation of the movable adjustment block 90 within the support block 78, which in turn causes pivoting movement of the head support surface 66 relative to the engagement structure 64. That is, turning the adjustment knob 94 translates the movable adjustment block 90 within slot 80, causing the head support surface 66 to be raised or lowered. In one embodiment, the adjustment knob 94 may be a single knob placed near the end of the assembly 60 (e.g., near the top of the patient's head) such that the know may be adjusted by an operator using one hand and from either side of the patient.

In implementations employing a threaded adjustment mechanism, as discussed herein, certain advantages may be realized. For example, one advantage of using such a threaded adjustment mechanism is the ability to adjust the tilt of the patient's head without having the patient lift their head or move (since the support is not being re-positioned between pre-determined, set positions). Further, a threaded adjustment mechanism as described herein is self-locking in both directions (i.e., up or down) due to the screw pitch and remains in place if the patient moves (e.g., lifts his or her head while strapped to the support 60) during the examination. Further, by using a threaded adjustment mechanism, the support assembly 60 may provide fine variable adjustment that allows for an exact angle (e.g., the best or optimal angle) from among a continuous range of supported head tilt angles (e.g., from 0° to 30° or −10° to 35°) to be configured by the operator, without being limited to pre-defined tilt positions (e.g., set positions at 5° increments). Though pre-defined tilt positions may not be structurally enforced (such as via notches or other mechanical features), the support assembly 60 may be marked (such as via markings (e.g., tilt angle markers or measurements) on the support block 78 and/or movable adjustment block 90) to allow an operator to select and/or repeat a tilt angle or inclination for patient head positioning. In this manner, a CT technologist can record the angle used for each patient and return the support 60 to that angle in future imaging sessions, while still retaining a full range of adjustment as opposed to pre-defined positions.

In certain embodiments employing a threaded adjustment mechanism, the sharp edges and/or composition (typically metallic) associated with the threading of the movable adjustment block 90 and the adjustment thread 92 may lead to image artifacts if present within the imaging volume during imaging. Hence, as shown in certain of the described embodiments, the movable adjustment block 90 and adjustment thread 92 (and the support block 78 in general) may be positioned outside the imaged volume when performing a head or brain scan. That is, present implementations keep the support block 78 and associated components (e.g., the threaded adjustment mechanism) out of the imaging path when performing a tilted head or brain scan to avoid or reduce image quality issues attributable to the tilt adjustment mechanism. Because other materials used in the head support assembly 60 may be fabricated using non-metallic materials, the head region through the neck region of a patient may be scanned using the assembly 60 without degrading image quality.

Figure 6:
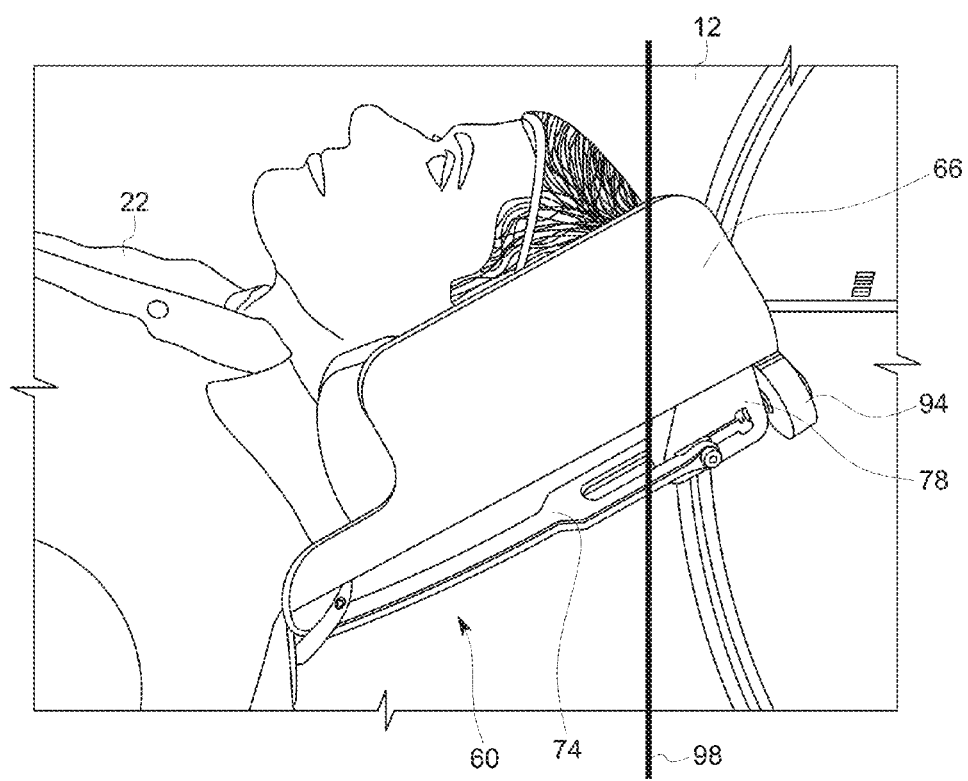
FIG. 6 depicts a patient's head supported by a tilted head support assembly as discussed herein, in accordance with aspects of the present description.
Figure 7:
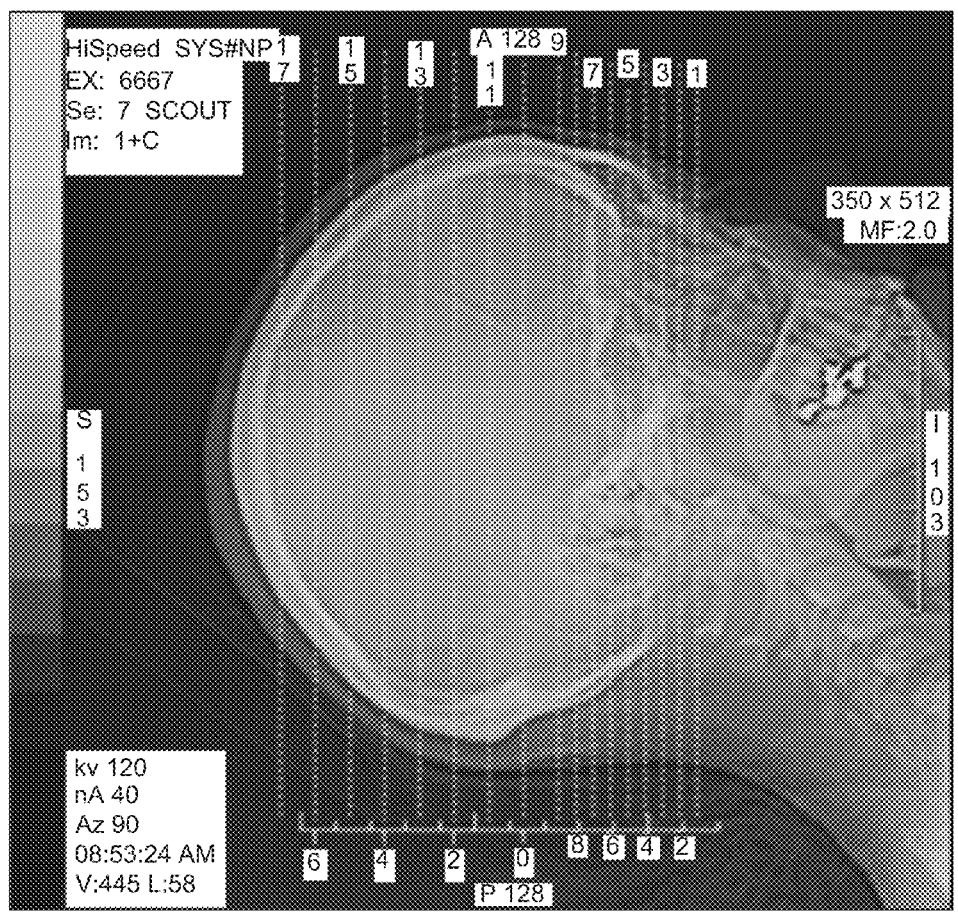
FIG. 7 depicts a tilted head image generated of a patient using a tilted head support assembly as discussed herein, in accordance with aspects of the present description.

An example, of the head support assembly 60 when in use and the placement of the support block 78, and threaded adjustment mechanism outside of the imaging path can be seen in FIGS. 6 and 7. As shown in FIG. 6, a patient 22 whose head is supported by the head support assembly 60 is not within a vertical plane (see vertical demarcation line 98) in which the support block 78 and adjustment mechanism components are also present. This can also be seen in FIG. 7, depicting an image generated using a head support assembly to tilt a patient's head during imaging. In this example, the top of the patient's head is not vertically in line with the metallic or sharp-edged components of the head support assembly 60, and thus artifacts due to these components are avoided. Further, the image of FIG. 7 also illustrates that, by introducing tilt by means of a head support as discussed herein, X-ray dose directed toward the patient's eyes may be avoided or reduced.

With the preceding description and discussion in mind, it should be appreciated that present embodiments of a tilting head support for use in medical imaging allow a patient to receive the equivalent of a tilted gantry exam study, which provides the best imaging of the brain and little or no X-ray dose to the eyes, even when using a scanner gantry that does not tilt. Further, if during the tilted head exam it is determined that the scan should continue down through the neck region, or even onwards, the patient can be scanned in the present tilted head support as there is no part of the adjustment mechanism present in the imaging region.

Technical effects of the invention include a tilted head support assembly having metallic or sharp edge components positioned outside the imaging area when in use. Technical effects also include a tilted head support assembly that allows for selection of a tilt angle from among a continuous range of available angles and user adjustment of the angle even when the patient's head is resting on the support assembly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A head support attachment for use in image acquisition, comprising:
    an engagement structure configured to removably attach the head support attachment to an end of a patient support table;
    a head support surface pivotally connected to the engagement structure at a first end of the head support surface;
    an adjustment arm pivotally connected at a first end to the engagement structure and slidably engaged with the head support surface at a second end of the adjustment arm;
    an adjustment mechanism comprising a threaded assembly configured to adjust the position of the second end of the adjustment arm so as to determine the position of the adjustment arm relative to the head support surface;
    wherein the adjustment arm is slidably engaged with the head support surface and connected to a movable adjustment block, and wherein the threaded assembly comprises an adjustment knob configured to rotate a threaded member that moves the movable adjustment block when the adjustment knob is rotated.

2. The head support attachment of claim 1, wherein the engagement structure comprises an insertable engagement structure configured to insert into a complementary slot formed in the end of the patient support table.

3. The head support attachment of claim 1, wherein the engagement structure forms a cantilevered interface when the head support attachment is attached to the end of the patient support table.

4. The head support attachment of claim 1, wherein the head support surface is configured to pivot within a range of about −10° to about 35° with respect to the engagement structure.

5. The head support attachment of claim 1, wherein the head support surface is configured to pivot within a range of about 0° to about 30° with respect to the engagement structure.

6. The head support attachment of claim 1, wherein the movable adjustment block is configured to move within a slot formed in a support block attached to or formed on the head support surface.

7. The head support attachment of claim 1, wherein the position of the second end of the adjustment arm within the slot determines the tilt of the head support surface.

8. The head support attachment of claim 1, wherein the adjustment knob is accessible from either side of the patient support table.

9. The head support attachment of claim 1, wherein the adjustment mechanism, when in use, is outside of a volume imaged during an image acquisition and the head support and adjustment arm are within the volume.

10. The head support attachment of claim 1, wherein the adjustment mechanism is fabricated from metal and the engagement structure, head support surface, two pivot pins, and adjustment arm fabricated from one or more of plastic or carbon fiber.

11. A head support attachment for use in image acquisition, comprising:
    a head support surface comprising an imaged region and a non-imaged region, the imaged region comprising a first pivoting engagement and the non-imaged region comprising a sliding engagement;
    a table engagement structure attached to the head support surface at the first pivoting engagement such that the head support surface pivots relative to the table engagement structure at the first pivoting engagement;
    an adjustment arm attached to the table engagement structure at a second pivoting engagement and attached to the head support surface at the sliding engagement; and
    an adjustment mechanism underlying the non-imaged region of the head support surface, the adjustment mechanism comprising an adjustment thread configured to move a movable adjustment block within the sliding engagement, wherein the position of the movable adjustment block adjusts the position of the adjustment arm within the sliding engagement to control the tilt of the head support surface relative to the table engagement structure.

12. The head support attachment of claim 11, wherein the sliding engagement comprises a slot formed within a support block of the head support surface.

13. The head support attachment of claim 11, wherein the table engagement structure comprises an insertable engagement configured to be inserted into a complementary opening at the end of a patient support table.

14. The head support attachment of claim 11, wherein the adjustment mechanism comprises an adjustment knob configured to turn the adjustment thread.

15. The head support attachment of claim 11, wherein the adjustment mechanism is fabricated from metal and the engagement structure, head support surface, two pivot pins, and adjustment arm fabricated from one or more of plastic or carbon fiber.

16. The head support attachment of claim 11, wherein the head support surface is configured to pivot within a range of about −10° to about 35° with respect to the table engagement structure.

17. A patient support, comprising:
   a support table comprising a first end and a second end; and
   a head support attached to the first end of the support table, the head support comprising:
      an engagement structure configured to attach to the first end of the support table;
      a head support surface comprising an imaged region proximate to the support table and a non-imaged region distal from the support table, the imaged region comprising a first pivoting engagement to the engagement structure and the non-imaged region comprising a sliding engagement;
      an adjustment arm pivotally connected at a first end to the engagement structure and attached to the head support surface at the sliding engagement; and
      an adjustment mechanism underlying the non-imaged region of the head support surface, the adjustment mechanism comprising an adjustment thread configured to move a movable adjustment block within the sliding engagement, wherein the position of the movable adjustment block adjusts the position of the adjustment arm within the sliding engagement to control the tilt of the head support surface relative to the support table.

18. The patient support table of claim 17, wherein the engagement structure comprises an insertable engagement configured to be inserted into a complementary opening at the first end of the support table.

19. The patient support table of claim 17, wherein the head support surface is configured to pivot within a range of about −10° to about 35° with respect to the support table.

20. The patient support table of claim 17, wherein the engagement structure forms a cantilevered interface when the head support is attached to the first end of the support table.

* * * * *